US006998489B2

(12) United States Patent
Conrow et al.

(10) Patent No.: US 6,998,489 B2
(45) Date of Patent: Feb. 14, 2006

(54) METHODS OF MAKING INDAZOLES

(75) Inventors: Raymond E. Conrow, Crowley, TX (US); Pete Delgado, Fort Worth, TX (US); William D. Dean, Arlington, TX (US); David R. Pierce, Fort Worth, TX (US); Michael S. Gaines, Fort Worth, TX (US)

(73) Assignee: Alcon, Inc., Hünenberg (CH)

( * ) Notice: Subject to any disclaimer, the term of this patent is extended or adjusted under 35 U.S.C. 154(b) by 80 days.

(21) Appl. No.: 10/723,297

(22) Filed: Nov. 26, 2003

(65) Prior Publication Data

US 2004/0142998 A1 Jul. 22, 2004

Related U.S. Application Data

(63) Continuation of application No. PCT/US02/17115, filed on May 30, 2002, and a continuation-in-part of application No. PCT/US02/16843, filed on May 30, 2002.

(60) Provisional application No. 60/295,430, filed on Jun. 1, 2001, provisional application No. 60/295,427, filed on Jun. 1, 2001.

(51) Int. Cl.
*C07D 231/56* (2006.01)
(52) U.S. Cl. .................................................. 548/362.5
(58) Field of Classification Search .............. 548/362.5
See application file for complete search history.

(56) References Cited

FOREIGN PATENT DOCUMENTS

WO    WO 98/30548     7/1998
WO    WO 02/098861 A1   12/2002

OTHER PUBLICATIONS

Supplementary European Search Report for EP Application No. 02737285.3 dated Sep. 6, 2004.
Akazome et al., "Palladium Complex-Catalyzed Reductive N-Heterocyclization of Nitroarenes: Novel Synthesis of Indole and 2H-Indazole Derivatives," J. Org. Chem., vol. 59, No. 12, 1994, pp. 3375-3380.
Matassa et al., "Evolution of a Series of Peptidoleukotriene Antagonists: Synthesis and Structure/Activity Relationships of 1,3,5-Substituted Indoles and Indazoles" J. Med. Chem., vol. 33, pp. 1781-1790 (1990).
Brown et al., "1,3,6-Trisubstituted Indoles as Peptidoleukotriene Antagonists: Benefits of a Second, Polar, Pyrrole Substituent," J. Med. Chem., vol. 35, pp. 2419-2439 (1992).
Fischer et al., "Ueber die Hydrazine der Zimmtsaure" Justus Liebigs Annalen der Chemie, vol. 227, pp. 302-341 (1884).
Applegate et al., "The Efficient Synthesis of 3-Arylsydnones Under Neutral Conditions," Synthesis, pp. 1011-1012, (1988).
McGeachin, "The Structures of Two Self-Condensation Products from o-Aminobenzaldehyde," Canadian Journal of Chemistry, vol. 44, pp. 2323-2328, (1966).
Caron et al., "A Versatile and Efficient Synthesis of Substituted 1H-Indazoles," Synthesis, No. 4, pp. 588-592 (1999).
Halley et al., "Synthesis of 5-Cyanoindazole and 1-Methyl and 1-Aryl-5-Cyanoindazoles," Synthetic Communications, vol. 27, pp. 1199-1207, (1997).
Suwinski et al., "The Mechanism of Elimination of Aldoxime Hydrogensulfates to Nitriles," Polish Journal of Chemistry, vol. 59, pp. 521-529, (1985).
von Auwers et al., "Uber Synthesen von N-Acyl-indazolen," Justus Liebigs Annalen der Chemie, vol. 450, pp. 273-303, (1926).
Al-Khamees et al., "Synthesis of (±)-(4aS, 13cR)- and (±)-(4aR, 13cR)-1,2,3,4,4a, 13c-Hexahydro-5H-indazolo[2,3-d][1,4] benzodiazepine-6(7H)-ones," Journal of the Chemical Society, Perkin Trans. 1, pp. 2001-2006, (1985).
Fieser et al., "Nickel catalysts (a), Raney type," Reagents for Organic Synthesis, vol. 1, p. 723-731, (1967).
Song et al., "A Novel Synthesis of 2-Aryl-2H-indazoles via a Palladium-Catalyzed Intramolecular Amination Reaction," Organic Letters, vol. 2, No. 4, pp. 519-521, (2000).
Maeno et al., "Preparation of aminoalkylindazole derivatives as 5-HT2c receptor agonists," WO 9830548, Jul. 16, 1998, abstract. Database CAPLUS on STN, Accession No. 1998:490629, vol. 129, No. 136164.
International Search Report for PCT/US02/17115 dated May 30, 2002.
International Search Report for PCT/US02/16843 dated May 30, 2002.

*Primary Examiner*—Taofiq Solola
(74) *Attorney, Agent, or Firm*—Kilyk & Bowersox, P.L.L.C.

(57) ABSTRACT

Methods of making indazoles are described. The methods involved reacting an aromatic aldehyde with a nitrogen source to form a nitroso aromatic aldehyde. The nitroso aromatic aldehyde is reacted with a reducing agent to form an indazole which ultimately can be used to form desired indazoles which are preferably pharmaceutically active products. The process of the present invention further permits the formation of enantiomerically enriched or pure indazoles such as aminoalkyl indazoles.

22 Claims, No Drawings

METHODS OF MAKING INDAZOLES

This application is a continuation of International Patent Application No. PCT/US02/17115 filed May 30, 2002 and in turn claims the benefit of U.S. Provisional Patent Application No. 60/295,430, filed Jun. 1, 2001, and is incorporated in its entirety by reference herein, and is also a continuation in part of International Patent Application No. PCT/US02/16843 filed May 30, 2002 and in turns claims the benefit of U.S. Provisional Patent Application No. 60/295,427 filed Jun. 1, 2001, and is incorporated in its entirety by reference herein.

BACKGROUND OF THE INVENTION

The present invention relates to methods of making indazoles and more particularly relates to methods of making indazoles which avoid unwanted by-products and results in enantiomerically pure final pharmaceutically active products.

WO 98/30548 (Yamanouchi) shows the utility of 1-(aminoalkyl)indazoles for treating CNS diseases. The route of synthesis involves the reaction of various indazoles, having substituents only in the benzene ring, with alkylating agents. It is well known that such alkylation of indazoles always gives about a 1:1 mixture of isomeric 1- and 2-alkylindazoles. See, generally, Song and Yee, Organic Letters, vol. 2, page 519 (2000). Therefore about half of the reaction material is wasted due to the formation of the undesired 2-alkylindazole which must be separated by chromatography or other technique. The isolated 1-alkylindazole is then further modified to provide the target 1-(aminoalkyl)indazole.

Fischer and Tafel, Justus Liebigs Annalen der Chemie, vol. 227, p. 334 (1885) report nitrosation of 2'-ethylaminoacetophenone with sodium nitrite and the reduction of the resulting nitrosamine with zinc to yield 1-ethyl-3-methylindazole. Use of isoamyl nitrite instead of sodium nitrite for an analogous nitrosation is discussed in Applegate and Turnbull, Synthesis, p. 1011 (1988). McGeachin, Canadian Journal of Chemistry, vol. 44, p. 2323 (1966) reports nitrosation of a 2-aminobenzaldehyde wherein the amino group is substituted with a nonhydroxylic $C_{23}H_{18}N_3O$ group, for the purpose of verification of chemical structure. The resulting nitrosamine was reduced with zinc forming a very specific indazole, for the purpose of further verification of chemical structure.

Monoalkylhydrazines react with benzophenones or acetophenones having ortho leaving groups (e.g., halide or mesylate) to give 1-alkylindazoles substituted at the 3-position as reported in Caron and Vazquez, Synthesis, p. 588 (1999). The analogous conversion of benzaldehydes to 3-unsubstituted indazoles requires forcing conditions unsuitable for scaleup. See Halley and Sava, Synthetic Communications, vol. 27, p. 1199 (1997).

Suwinski and Walczak, Polish Journal of Chemistry, vol. 59, p. 521 (1985), report cyclization of 2-aminobenzaldoxime hemisulfate to give indazole. The inventors attempted to extend this method to a 2-alkylaminobenzaldoxime hemisulfate, but the desired 1-alkylindazole was not obtained and instead the unwanted nitrile or the free oxime was obtained. An analogous cyclization of oxime acetates, demonstrated only for forming 3-substituted indazoles, employs conditions poorly suited for scaleup as shown in Brown et al., Journal of Medicinal Chemistry, vol. 35, p. 2419 (1992). Cyclization of 2-acylaminobenzaldoxime derivatives yields 1-acylindazoles (von Auwers and Frese, Justus Liebigs Annalen der Chemie, vol. 450, p. 290 (1926)) but these do not provide 1-alkylindazoles upon reduction, the 1-unsubstituted indazole being formed instead. See Al-Khamees and Grayshan, Journal of the Chemical Society, Perkin Trans. I, p. 2001 (1985). A known synthesis of 1,3-dialkylindazoles from 1,3-dialkylindoles involves (1) oxidative cleavage of the 1,3-dialkylindazole to give the 2-(N-alkylformamido)aryl alkyl ketone; (2) ketoxime formation with concurrent N-deformylation; (3) O-acetylation; and (4) heating the resulting ketoxime acetate at 170–200° C. in the melt, under vacuum. See Matassa et al., J. Med. Chem., vol. 33, page 1781 (1990); and Brown et al., J. Med. Chem., vol. 35, page 2419 (1992). This method has not been demonstrated for aldoximes, required for the synthesis of 3-unsubstituted indazoles. Furthermore, the in vacuo thermolysis step has been reported on a maximal 1.3-gram scale, and would present experimental difficulties on a larger preparative scale.

Accordingly, there is a need to provide processes to manufacture 1-(aminoalkyl)indazoles which avoid undesired isomers and which are capable of producing large quantities of the desired compound.

All patents, patent applications, and publications referenced in this application are incorporated in their entirety and form a part of the present application.

SUMMARY OF THE PRESENT INVENTION

A feature of the present invention is to provide a method to make indazoles such as hydroxy indazoles.

A further feature of the present invention is to provide a method to make indazoles in large quantities and with avoiding large quantities of undesired isomers.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages and in accordance with the purposes of the present invention, as embodied and properly described herein, the present invention relates to a method of making an indazole involving:

a) the nitrosation of an aromatic aldehyde to form a nitroso aromatic aldehyde; and b) reacting said nitroso aromatic aldehyde with a reducing agent to form an indazole.

In the present invention, the method of making an indazole can further include the steps of reacting the indazole from step (b) above with a sulfonyl halide or anhydride to form the corresponding sulfonic ester. The method can then involve reacting this corresponding sulfonic ester with a metal azide to yield an azido indazole which can then be reacted with a hydrogen source and a catalyst to yield the desired aminoalkyl indazole.

Also, the present invention relates to a method of making an indazole involving:

a) nitrosating a 2-(hydroxyalkyl)aminobenzaldehyde to form a 2-(hydroxyalkyl)nitrosaminobenzaldehyde; and b) reacting said 2-(hydroxyalkyl)nitrosaminobenzaldehyde with a reducing agent to form a 1-(hydroxyalkyl) indazole.

In this embodiment, the method of making an indazole can further include the steps of reacting the 1-(hydroxyalkyl) indazole from step (b) above with a sulfonyl halide or sulfonic anhydride to form the corresponding sulfonic ester. The method can then involve reacting this sulfonic ester with a metal azide to yield a 1-(azidoalkyl)indazole which can then be reacted with a hydrogen source and a catalyst to yield the desired 1-(aminoalkyl)indazole.

It is to be understood that both the foregoing general description and the following detailed description are exemplary and explanatory only and are intended to provide a further explanation of the present invention, as claimed.

DETAILED DESCRIPTION OF THE PRESENT INVENTION

The present invention relates to methods of making indazoles. More particularly, the present invention involves making indazoles using aromatic aldehydes as the starting material. The indazoles that can be made following the methods of the present invention are preferably enantiomerically pure products which are preferably useful as pharmacologically active products such as in the treatment of glaucoma and/or are useful for lowering and controlling normal or elevated intraocular pressure.

In the methods of the present invention, indazoles can be produced by taking the starting aromatic aldehyde and forming a nitroso aromatic aldehyde by the nitrosation of the aromatic aldehyde. This nitroso aromatic aldehyde can then be reacted with a reducing agent to form an indazole. This indazole can then be further reacted to form a desired indazole which is preferably enantiomerically pure and is preferably a pharmaceutically active product. The indazole forming from the reaction between the nitroso aromatic aldehyde and reducing agent can be reacted with a sulfonyl hydride or anhydride to form a corresponding sulfonic ester. This sulfonic ester can be reacted with a metal azide to yield an azido indazole which in turn is reacted with a hydrogen source and a catalyst to yield an aminoalkyl indazole.

The starting aromatic aldehyde which is subjected to nitrosation can be any aromatic aldehyde that is capable of converting to a nitroso aromatic aldehyde. For instance, the aromatic aldehyde can have the formula Ar(CHO)(NHR). In this formula, R is —OH, an alkyl group, or an aromatic group. Ar is a substituted or unsubstituted aromatic group such as phenyl, aromatic sulfide, aromatic nitro group, and the like.

The aromatic aldehyde which is used in the methods of the present invention can be prepared by any number of reaction schemes. For instance, the aromatic aldehyde can be formed from reacting an indole with ozone in an organic solvent followed by addition of at least one reducing agent to form a formyl aromatic aldehyde. The formyl aromatic aldehyde can be reacted with a base or acid in the presence of water and/or an organic solvent to yield the starting aromatic aldehyde. Alternatively, the aromatic aldehyde can be formed by starting with a benzonitrile which is reacted with a reactant that permits the attachment of desired substituents on the benzonitrile. For instance, fluorobenzonitrile can be reacted with 1-amino-2 propanol in the presence of an organic solvent to yield the desired 2-(hydroxypropyl) aminobenzonitrile. The benzonitrile can then be reacted with a hydrogen source and a catalyst to form the desired aromatic aldehyde.

Besides these reaction schemes, other reaction schemes can be used to form the desired starting aromatic aldehyde. Those skilled in the art, in view of the present invention, can form a variety of starting aromatic aldehydes for purposes of the present invention.

In the present invention, the method of making the desired indazole generally can occur at any temperature above the freezing point of the reactants. For instance, the method can occur at a temperature of from about 25° C. to about −25° C.

As shown in the details of the preferred embodiment set forth below, the nitrosation can be accomplished by the addition of at least one organic nitrite or inorganic nitrite preferably in the presence of at least one organic solvent. Examples of suitable nitrites include, but are not limited to, isoamyl nitrite or sodium nitrite. Preferred solvents include, but are not limited to, tetrahydrofuran, acetic acid, or an organic-aqueous solvent pair such as acetic acid-water or tetrahydrofuran-dilute aqueous HCl. Combinations or mixtures of two or more nitrites can be used. This would also be true with respect to the other reactants in that combinations or mixtures of various reactants can be used.

Preferably, the reducing agent used above is a metal such as zinc. Other reducing agents known to those skilled in the art can be used. The catalyst that is used in the methods of the present invention is preferably palladium on charcoal in the presence of a solvent which is an organic solvent like ethanol. The hydrogen source can be any hydrogen source such as an ammonium formate. Another example of a suitable solvent is an acetic acid.

Depending on the starting aromatic aldehyde, the desired indazoles such as the aminoalkyl indazole can be formed. As shown in the preferred embodiment and in the examples, the present invention essentially prevents the formation of unwanted isomers thus resulting in improved yields and a process that is less expensive. The process of the present invention can essentially start with racemic mixtures of the starting aromatic aldehyde or can start with optically pure starting materials such as (R) aromatic aldehydes or (S) aromatic aldehydes. Thus, the process of the present invention permits great flexibility in the starting aromatic aldehydes which further permits great flexibility in forming various desired indazoles such as aminoalkyl indazoles. The indazoles which can be formed using the methods of the present invention are useful in, for instance, treating glaucoma and/or lowering or controlling elevated intraocular pressure. Examples of such uses for indazoles include those set forth in International Published Application WO 98/30548 and other patents and publications mentioned herein.

The process of the present invention which permits the use of an aromatic aldehyde typically uses an amino group on the benzaldehyde. This amino group can be substituted or unsubstituted and as shown in one of the preferred aromatic aldehyde formulas, the amino group can be NHR where the R is OH, alkyl group, or aromatic group. The ability to have a substituted amino group in such a reaction is a great benefit and unexpected since those skilled in the art might expect that the unprotected OH group would not survive further processing. However, as shown in the examples, the ability to have an unprotected OH group on the benzaldehyde can be done and ultimately that hydroxy group can be present for the ultimate end product which is preferably an aminoalkyl indazole. Thus, the present invention permits the formation of various desirable indazoles, which previous to the present process, were quite difficult to form.

In a more specific and preferred embodiment, the present invention involves making 1-(aminoalkyl)indazoles using 2-(hydroxyalkyl)aminobenzaldehydes as the starting material. The 1-(aminoalkyl)indazoles that can be made following the methods of the present invention are preferably enantiomerically pure products which are preferably useful as pharmacologically active products such as in the treatment of glaucoma and/or are useful for lowering and controlling normal or elevated intraocular pressure.

In a preferred embodiment of the present invention, indazoles can be produced by nitrosating a 2-(hydroxyalkyl) aminobenzaldehyde to form a 2-(hydroxyalkyl)nitrosaminobenzaldehyde. This 2-(hydroxyalkyl)nitrosaminobenzaldehyde can be reacted with a reducing agent to form a 1-(hydroxyalkyl)indazole. Preferably, the reducing agent is a metal such as zinc. Other reducing agents known to those skilled in the art can be used. This 1-(hydroxyalkyl)indazole can then be further reacted to form a desired 1-(aminoalkyl) indazole which is preferably enantiomerically pure and is preferably a pharmaceutically active product. The 1-(hydroxyalkyl)indazole can be reacted with a sulfonyl halide or sulfonic anhydride to form a corresponding sulfonic ester. This sulfonic ester can be reacted with a metal azide to yield a 1-(azidoalkyl)indazole which in turn is reacted with a hydrogen source and a catalyst to yield a 1-(aminoalkyl) indazole. The hydrogen source is preferably ammonium formate and the catalyst is preferably palladium on charcoal in the presence of an organic solvent like ethanol.

Preferably, the 2-(hydroxyalkyl)aminobenzaldehyde has the formula

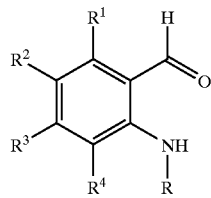

In this formula, R is a $C_2$ to $C_{12}$ alkyl group substituted with at least one OH group and optionally substituted with phenyl, methoxyphenyl, (dimethylamino)phenyl, $OR^5$, $OC(=O)R^5$, $OC(=O)OR^5$, $N(R^5)_2$, $N(R^5)C(=O)R^5$, $N(R^5)C(=O)OR^5$, or with one or more F atoms; $R^1$, $R^2$, $R^3$ and $R^4$ are independently H, F, Cl, Br, $CF_3$, OH, $OR^5$, $OC(=O)R^5$, $OC(=O)OR^5$, $N(R^5)_2$, $N(R^5)C(=O)R^5$, $N(R^5)C(=O)OR^5$, $NO_2$, CN, $N_3$, SH, $S(O)_nR^5$, $C(=O)R^5$, COOH, $COOR^5$, $CON(R^5)_2$, $C_1$ to $C_6$ alkyl optionally substituted with phenyl, methoxyphenyl, (dimethylamino)phenyl, $C(=O)R^5$, COOH, $COOR^5$, $CON(R^5)_2$, CN, $OR^5$, $OC(=O)R^5$, $OC(=O)OR^5$, $N(R^5)_2$, $N(R^5)C(=O)R^5$, or $N(R^5)C(=O)OR^5$; or $R^1$ and $R^2$ as herein defined taken together form a ring, or $R^2$ and $R^3$ as herein defined taken together form a ring, or $R^3$ and $R^4$ as herein defined taken together form a ring; $R^5$ is $C_1$ to $C_6$ alkyl optionally substituted with phenyl, methoxyphenyl, (dimethylamino)phenyl, methoxy, ethoxy, benzyloxy, or with one or more F atoms, or $R^5$ is phenyl, methoxyphenyl, or (dimethylamino)phenyl; and n=0, 1, or 2.

More preferably, R is a $C_2$ to $C_6$ alkyl group substituted with at least one OH group and optionally substituted with phenyl, $OR^5$, $N(R^5)C(=O)R^5$, $N(R^5)C(=O)OR^5$, or with one or more F atoms; $R^1$, $R^2$, $R^3$ and $R^4$ are independently H, F, Cl, $CF_3$, $OR^5$, $OC(=O)R^5$, $OC(=O)OR^5$, $N(R^5)_2$, $N(R^5)C(=O)R^5$, $N(R^5)C(=O)OR^5$, $NO_2$, CN, $C(=O)R^5$, $COOR^5$, $CON(R^5)_2$, $C_1$ to $C_6$ alkyl optionally substituted with phenyl, $C(=O)R^5$, $COOR^5$, $CON(R^5)_2$, CN, $OR^5$, $OC(=O)R^5$, $OC(=O)OR^5$, $N(R^5)_2$, $N(R^5)C(=O)R^5$, or $N(R^5)C(=O)OR^5$; or $R^1$ and $R^2$ as herein defined taken together form a ring, or $R^2$ and $R^3$ as herein defined taken together form a ring, or $R^3$ and $R^4$ as herein defined taken together form a ring; $R^5$ is $C_1$ to $C_6$ alkyl optionally substituted with phenyl, methoxyphenyl, methoxy, benzyloxy, or with one or more F atoms, or $R^5$ is phenyl or methoxyphenyl.

The 2-(hydroxyalkyl)aminobenzaldehyde which is preferably used in the methods of the present invention can be prepared by any number of reaction schemes. For instance, the 2-(hydroxyalkyl)aminobenzaldehyde can be formed by reacting a 1-(hydroxyalkyl)indole with ozone in an organic solvent followed by addition of at least one reducing agent to form a 2-(N-(hydroxyalkyl)formamido)benzaldehyde. The 2-(N-(hydroxyalkyl)formamido)benzaldehyde can be reacted with a base or acid in the presence of water and/or an organic solvent to yield the 2-(hydroxyalkyl)aminobenzaldehyde. Alternatively, the 2-(hydroxyalkyl)aminobenzaldehyde can be formed by starting with a 2-fluorobenzonitrile. The 2-fluorobenzonitrile can be reacted with a (hydroxyalkyl)amine to yield a 2-(hydroxyalkyl)aminobenzonitrile. For instance, a 2-fluorobenzonitrile can be reacted with 1-amino-2-propanol in the presence of an organic solvent to yield the desired 2-(2-hydroxypropyl)aminobenzonitrile. The 2-(2-hydroxypropyl)aminobenzonitrile can then be reacted with a hydrogen source and a catalyst to form the desired 2-(hydroxyalkyl)aminobenzaldehyde.

Besides these reaction schemes, other reaction schemes can be used to form the desired starting 2-(hydroxyalkyl) aminobenzaldehyde. Those skilled in the art, in view of the present invention, can form a variety of starting 2-(hydroxyalkyl)aminobenzaldehydes for purposes of the present invention.

As shown in the details of the preferred embodiment set forth below, the nitrosation can be accomplished by the addition of at least one organic nitrite or inorganic nitrite preferably in the presence of at least one organic solvent. Examples of suitable nitrites include, but are not limited to, isoamyl nitrite or sodium nitrite. Preferred solvents include, but are not limited to, tetrahydrofuran, acetic acid, or an organic-aqueous solvent pair such as acetic acid-water or tetrahydrofuran-dilute aqueous HCl. Combinations or mixtures of two or more nitrites can be used. This would also be true with respect to the other reactants in that combinations or mixtures of various reactants can be used.

Depending on the starting 2-(hydroxyalkyl)aminobenzaldehyde, desired indazoles such as 1-(aminoalkyl)indazoles can be formed. As shown in the preferred embodiment and in the examples, the present invention prevents the formation of unwanted isomers thus resulting in improved yields and a process that is less expensive. The process of the present invention can start with a racemic 2-(hydroxyalkyl) aminobenzaldehyde, or can start with an enantiomerically enriched or enantiomerically pure 2-(hydroxyalkyl)aminobenzaldehyde of either R or S configuration. Thus, the process of the present invention permits great flexibility in the starting 2-(hydroxyalkyl)aminobenzaldehyde, which further permits great flexibility in forming various desired indazoles such 1-(aminoalkyl)indazoles. The indazoles which can be formed using the methods of the present invention are useful in, for instance, treating glaucoma and/or lowering or controlling elevated intraocular pressure.

The process of the present invention preferably uses a 2-(hydroxyalkyl)aminobenzaldehyde. The ability to carry an unprotected hydroxy group through such a reaction sequence is a great benefit and unexpected since those skilled in the art might expect that the hydroxy group would not survive the reaction sequence. However, as shown in the examples, the hydroxy group can be present, without the need for a protecting group, for use in forming the end product which is preferably a 1-(aminoalkyl)indazole. Thus, the present invention permits the formation of various desirable indazoles, which previous to the present process, were quite difficult to form.

With respect to the preferred reactants and the preferred reaction schemes, set forth below and in Scheme 1 are preferred reaction schemes in the formation of a preferred 2-(hydroxyalkyl)aminobenzaldehyde which is then subsequently subjected to preferred reactions in the formation of the indazole. While the preferred components are set forth below, it is to be recognized that the present invention embraces other reactants, which in view of the present application, can easily be used by those skilled in the art.

Sequence A:

Step 1. 6-Benzyloxyindole (1) (Batcho and Leimgruber, Organic Syntheses, Collective Vol. 7, p. 34 (1990)) is reacted with (±)-propylene oxide and a base in an organic solvent to yield (±)-1-(2-hydroxypropyl)-6-benzyloxyindole (2). Preferably the base is sodium hydride and the solvent is tetrahydrofuran. The temperature is 0° C. to 25° C., preferably about 10° C. Preferably an inert atmosphere, e.g., nitrogen or argon, is maintained.

Alternatively, compound 1 is reacted with (R)-propylene oxide according to the foregoing method to yield (R)-1-(2-hydroxypropyl)-6-benzyloxyindole (R-2). Alternatively, compound 1 is reacted with (S)-propylene oxide according to the foregoing method to yield (S)-1-(2-hydroxypropyl)-6-benzyloxyindole (S-2).

Step 2. Compound 2 is reacted with ozone in an organic solvent, preferably dichloromethane, at −80 to −40° C., preferably −55 to −70° C., followed by addition of a reducing agent, preferably dimethyl sulfide. The temperature is then allowed to increase to about 25° C., to yield (±)-4-benzyloxy-2-(N-(2-hydroxypropyl)formamido)benzaldehyde (3).

Alternatively, compound R-2 is reacted according to the foregoing method to yield (R)-4-benzyloxy-2-(N-(2-hydroxypropyl)formamido)benzaldehyde (R-3). Alternatively, compound S-2 is reacted according to the foregoing method to yield (S)-4-benzyloxy-2-(N-(2-hydroxypropyl)formamido)benzaldehyde (S-3).

Step 3. Compound 3 is reacted with a base or an acid in the presence of water and an organic solvent, to yield (±)-4-benzyloxy-2-(2-hydroxypropyl)aminobenzaldehyde (6). Preferably, base is used and the preferred base is sodium hydroxide or potassium hydroxide and the preferred solvent is tetrahydrofuran and the temperature is 0 to 35° C., preferably 20 to 25° C. Preferably, an inert atmosphere, e.g., nitrogen or argon, is maintained.

Alternatively, compound R-3 is reacted according to the foregoing method to yield (R)-4-benzyloxy-2-(2-hydroxypropyl)aminobenzaldehyde (R-6). Alternatively, compound S-3 is reacted according to the foregoing method to yield (S)-4-benzyloxy-2-(2-hydroxypropyl)aminobenzaldehyde (S-6).

Sequence B:

Step 1. 4-Benzyloxy-2-fluorobenzonitrile (4) is reacted with (±)-1-amino-2-propanol in an organic solvent, to yield (±)-4-benzyloxy-2-(2-hydroxypropyl)aminobenzonitrile (5). At least two molar equivalents of 1-amino-2-propanol are used, as one molar equivalent is consumed as the amine hydrofluoride. Alternatively an auxiliary base is employed, for example a tertiary amine such as triethylamine or N,N-diisopropylethylamine, an alkali metal carbonate such as sodium carbonate or potassium carbonate, or basic alumina. When the auxiliary base is employed, less than two molar equivalents of (±)-1-amino-2-propanol can be used, preferably about 1.5 molar equivalents. Preferably an auxiliary base is employed, most preferably basic alumina. The solvent is preferably a dipolar aprotic solvent, for example dimethyl sulfoxide or N-methylpyrrolidone. The temperature is 80 to 140° C., preferably 100 to 120° C. Optionally, a drying agent, e.g., zeolite molecular sieves, is present.

Alternatively, compound 4 is reacted with (R)-1-amino-2-propanol according to the foregoing method to yield (R)-4-benzyloxy-2-(2-hydroxypropyl)aminobenzonitrile (R-5). Alternatively, compound 4 is reacted with (S)-1-amino-2-propanol according to the foregoing method to yield (S)-4-benzyloxy-2-(2-hydroxypropyl)aminobenzonitrile (S-5).

Step 2. Compound 5 is reacted with a hydrogen source and a catalyst in a solvent mixture containing water, an acidic component and an organic solvent, to yield (±)-4-benzyloxy-2-(2-hydroxypropyl)aminobenzaldehyde (6). The organic solvent can be formic acid, which also serves as the acidic component and hydrogen source, or acetic acid, which also serves as the acidic component. Optionally an organic co-solvent can be used, for example pyridine. The hydrogen source can be, for example, hydrogen gas, hypophosphorous acid, or an inorganic hypophosphite salt such as sodium hypophosphite. Preferably the solvent is a mixture of pyridine, acetic acid, and water in a ratio of about 2:1:1 parts by volume. Preferably, the hydrogen source is sodium hypophosphite and preferably the catalyst is Raney nickel. The temperature is 20 to 60° C., preferably 40 to 45° C.

[This method is generally described in Fieser and Fieser, Reagents for Organic Synthesis, Volume 1, page 726 (1967).]

Alternatively, compound R-5 is reacted according to the foregoing method to yield (R)-4-benzyloxy-2-(2-hydroxypropyl)aminobenzaldehyde (R-6). Alternatively, compound S-5 is reacted according to the foregoing method to yield (S)-4-benzyloxy-2-(2-hydroxypropyl)aminobenzaldehyde (S-6).

Compound 6 is reacted with an organic nitrite, e.g., isoamyl nitrite, in an organic solvent (e.g., tetrahydrofuran), or with an inorganic nitrite, e.g., sodium nitrite, in an organic solvent (e.g., acetic acid), or organic-aqueous solvent pair (e.g., acetic acid-water; tetrahydrofuran-dilute aqueous HCl) to yield (±)-4-benzyloxy-2-(2-hydroxypropyl)nitrosaminobenzaldehyde (7). Preferably the nitrite is sodium nitrite and the solvent is acetic acid-water. Preferably the temperature is kept between about 0° C. and 35° C. Preferably an inert atmosphere, e.g., nitrogen or argon, is maintained. The preferred method is to react 6 with about 1.2 molar equivalents of $NaNO_2$ in acetic acid-water (about 4:1 parts by volume) at 15 to 25° C. The resulting compound 7 can be isolated, but it is preferable instead to convert 7 without isolation to 8 e.g., by a one-flask method as described herein.

Alternatively, compound R-6 is reacted according to the foregoing method to yield (R)-4-benzyloxy-2-(2-hydroxypropyl)nitrosaminobenzaldehyde (R-7). Alternatively, compound S-6 is reacted according to the foregoing method to yield (S)-4-benzyloxy-2-(2-hydroxypropyl)nitrosaminobenzaldehyde (S-7).

Compound 7 is reacted with a reducing agent in an organic solvent optionally containing water to yield (±)-6-benzyloxy-1-(2-hydroxypropyl)indazole (8). Preferably the reducing agent is zinc and the solvent is a mixture of acetic acid and water in a ratio of about 4:1 parts by volume. Most preferably, the reduction is carried out by adding zinc to the reaction mixture in which compound 7 was prepared from compound 6, without isolation of compound 7.

The desired reduction-cyclization reaction of 7 to 8 can be accompanied by a competing denitrosation reaction to regenerate 6. When zinc dust is used as the reducing agent, the ratio of 8 to 6 is about 5:1. The nitrosation-reduction sequence can be repeated on the crude reaction mixture to effect nearly complete conversion of 6 to 8. Alternatively, removal of 6 from the crude product can be effected by chromatography. Alternatively, 6 is removed as a water-soluble hydrazone derivative which is formed by treating the crude product with, e.g., Girard's Reagent T or Girard's Reagent P. Alternatively, 6 is removed as a polymer-bound hydrazone derivative by treating the crude product with a polymer-bound arenesulfonylhydrazide resin.

Alternatively, compound R-7 is reacted according to the foregoing method to yield (R)-6-benzyloxy-1-(2-hydroxypropyl)indazole (R-8). Alternatively, compound S-7 is reacted according to the foregoing method to yield (S)-6-benzyloxy-1-(2-hydroxypropyl)indazole (S-8).

Compound 8 is reacted with an alkanesulfonyl halide or anhydride, or with an arenesulfonyl halide or anhydride, in an organic solvent in the presence of a base, to form the corresponding sulfonic ester. Preferably an alkanesulfonyl halide is used, most preferably methanesulfonyl chloride. The organic solvent can be pyridine which also serves as the base. Preferably the solvent is dichloromethane and the base is triethylamine. Preferably an inert atmosphere, e.g., nitrogen or argon, is maintained. The sulfonic ester thus obtained is reacted with an alkali metal azide in an organic solvent, to yield (±)-1-(2-azidopropyl)-6-benzyloxyindazole (9). Preferably the alkali metal azide is sodium azide and the solvent is preferably a dipolar aprotic solvent, most preferably N,N-dimethylformamide. The temperature can be 25 to 80° C., preferably about 60° C., and other temperatures are possible.

Alternatively, compound R-8 is reacted according to the foregoing method to yield (S)-1-(2-azidopropyl)-6-benzyloxyindazole (S-9). Alternatively, compound S-8 is reacted according to the foregoing method to yield (R)-1-(2-azidopropyl)-6-benzyloxyindazole (R-9).

Compound 9 is reacted with a hydrogen source and a catalyst in an organic solvent, to yield (±)-1-(2-aminopropyl)-6-hydroxy indazole (10). Preferably the hydrogen source is ammonium formate, the catalyst is palladium on charcoal and the solvent is ethanol.

Alternatively, compound S-9 is reacted according to the foregoing method to yield (S)-1-(2-aminopropyl)-6-hydroxy indazole (S-10). Alternatively, compound R-9 is reacted according to the foregoing method to yield (R)-1-(2-aminopropyl)-6-hydroxy indazole (R-10).

The following examples are given to illustrate the preparation of compounds that are the subject of this invention but should not be construed as implying any limitations to the claims.

EXAMPLES

Preparation of (±)-6-benzyloxy-1-(2-hydroxypropyl)indole (2). To a stirred, cooled (10° C.) suspension of NaH (80.7 g of a 60% dispersion in mineral oil, 2.02 mol) in anhydrous THF (1.9 L) was added a solution of 6-benzyloxyindole (1) (375 g, 1.68 mol) in anhydrous THF (1.9 L) keeping the temperature below 25° C. After 2 h at 10° C., (±)-propylene oxide (140 mL, 2.0 mol) was added dropwise keeping the temperature below 25° C. After 48 h at 10° C., (±)-propylene oxide (71 mL, 1.0 mol) was added. After 96 h at 10° C., saturated aqueous $KH_2PO_4$ (3.8 L) and ethyl acetate (3.8 L) were carefully added, the layers were separated and the aqueous solution was extracted with 3.8 L of ethyl acetate. The combined organic extracts were dried over sodium sulfate and concentrated in vacuo to yield 2 (520 g, 110%, contains mineral oil).

Preparation of (±)-4-Benzyloxy-2-(N-(2-hydroxypropyl)formamido)benzaldehyde (3). A solution of 172 g of 2 in 1.5 L of dichloromethane was cooled to 78° C. and ozonized (4% ozone in oxygen). Excess ozone was displaced with oxygen for 5 min, followed by addition of 78 mL of dimethyl sulfide and warming to 25° C. The solution was concentrated to half volume, eluted through Florisil rinsing with ethyl ether-ethyl acetate and concentrated in vacuo. One additional run on 172 g scale and three runs on 58-g scale were performed. The combined products were eluted through silica (2.5 kg) with a gradient of 10%-80% ethyl acetate-hexane to yield, after concentration in vacuo, 3 (351 g, 70%) as an oil.

Preparation of (±)-4-Benzyloxy-2-(2-hydroxypropyl)aminobenzaldehyde (6). An ice-cooled solution of 3 (298 g, 0.95 mol) in THF (3 L) was treated with 1 M aq NaOH (1.95 L, 1.9 mol) keeping the temperature below 80° C. After 3 was consumed, the mixture was diluted with brine and extracted twice with ethyl ether. The organic solution was washed with water until neutral and with brine, dried over sodium sulfate, treated with charcoal and eluted through silica (1 kg) with ether and with 1:1 ethyl acetate-hexane to yield, after concentration in vacuo, 6 (207 g, 76%) as a yellow solid.

Preparation of 4-Benzyloxy-2-fluorobenzonitrile (4). Benzyl bromide (467 mL, 3.93 mol) and potassium carbonate (1.4 kg, 10.1 mol) were added to a solution of 2-fluoro-4-hydroxybenzonitrile (490 g, 3.57 mol) in 3.4 L of acetone. The stirred mixture was heated at 60° C. for 20 h, then cooled and filtered. The filtrate was concentrated and the resulting solid was triturated with 10% ethyl acetate-hexane (5 L) and vacuum dried at 35° C. to yield 4 (787 g, 97%).

Preparation of (R)-4-Benzyloxy-2-(2-hydroxypropyl)aminobenzonitrile (R-5). A solution of (R)-(−)-1-amino-2-propanol (389 g, 5.19 mol) in DMSO (2.6 L) was added to a mixture of 4 (786 g, 3.46 mol), basic alumina (786 g), and 4A. molecular sieves (131 g). The stirred mixture was heated at 110–140° C. for 24 h, cooled and filtered through Celite, washing with 10 L of 4:1 ether-ethyl acetate followed by 4 L of 3:2 ethyl acetate-hexane. The organic washes were extracted with water (5 L) and the aqueous phase was extracted with four 2-L portions of 25% ethyl acetate-hexane. The combined organic phases were washed with water and brine, dried over sodium sulfate, concentrated to about 4 L and allowed to stand for 48 h. The precipitated solid was collected by filtration, washed with hexane and vacuum dried to provide R-5 (first crop 613 g, second crop, 86 g). The concentrated supernatant was applied to a 5 kg silica gel pad and eluted with a gradient of 10–50% ethyl acetate-hexane to give, after concentration in vacuo, 119 g of 5, for a total yield of 791 g (81%) of R-5.

Preparation of (R)-4-Benzyloxy-2-(2-hydroxypropyl)aminobenzaldehyde (R-6). Sodium hypophosphite hydrate (986 g, 11.2 mol) and Raney nickel (500 g of a 50% aqueous suspension) were added to a solution of R-5 (790 g, 2.8 mol) in 7 L of 2:1:1 pyridine-acetic acid-water. The mixture was stirred at 45° C. for 7 h, then cooled to 25° C. overnight and filtered through Celite rinsing with water and ethyl acetate. The filtrate was washed with saturated $Na_2HPO_4$ to pH 5, with water and brine, dried over sodium sulfate and concentrated. During concentration, 4 L of heptane was added to azeotropically remove pyridine. After 8 L of solvent had been removed the product solidified. Heptane (5 L) was added and the solid was triturated, isolated by filtration and vacuum dried at 35° C. to yield R-6 (722 g, 90%).

Preparation of (R)-6-benzyloxy-1-(2-hydroxypropyl)indazole (R-8). Sodium nitrite (209 g, 3.03 mol) was added over 25 min to a stirred solution of R-6 (720 g, 2.53 mol) in acetic acid (5.6 L) and water (1.4 L), keeping the temperature below 25° C. The resulting solution of nitrosamine R-7 was cooled in ice, and zinc dust (595 g, 9.10 mol) was added in 25-g portions over 3.5 h, keeping the temperature below 35° C. Ethyl acetate (7 L) was added and the thick suspension was filtered on a sintered glass funnel, washing with ethyl acetate (7.5 L). To the filtrate containing a 5:1 mixture of R-8 and regenerated R-6 was added Girard's Reagent T (98 g, 0.58 mol). After stirring at 25° C. for 1 day, another 150 g (0.90 mol) of Girard's Reagent T was added. After 3 more days R-6 was consumed. The mixture was extracted twice with water, with aqueous $Na_2HPO_4$ to remove acetic acid, with water and brine, dried over sodium sulfate, filtered through Florisil and concentrated. The residue was eluted through 5 kg of silica with 1:1 ethyl acetate-hexane. Clean fractions were concentrated and 4 L of heptane was added to precipitate R-8. The solid was collected by filtration, washed with 1:1 ethyl acetate-hexane and vacuum dried at 35° C. to yield (417 g, 58%) of a yellow solid, composed of 96.7% R-8, 0.3% S-8 and 3% R-6 by HPLC. Concentration of the supernatant afforded an additional 141 g (20%) of R-8.

Preparation of (±)-6-benzyloxy-1-(2-hydroxypropyl)indazole (8). The procedure described for R-8 was followed, beginning with (±)-6 (202.7 g, 0.71 mol). After nitrosamine 7 had been converted to a mixture of 8 and 6 (5:1), sodium nitrite (29.5 g, 0.43 mol) was added to renitrosate 6. Zinc dust (84 g, 1.28 mol) was then added in portions with cooling as described above. When the formation of 8 was complete, the reaction mixture was worked up as described above and combined with the product from another run that started with 176 g of 6. The combined crude product was purified by chromatography on a Biotage Kiloprep-250 instrument, eluting with ethyl acetate-hexane, to yield 8 (226 g, 60%) of 99% HPLC purity.

Preparation of (S)-1-(2-Azidopropyl)-6-benzyloxyindazole (S-9). A solution of R-8 (415 g, 1.47 mol) in dichloromethane (4 L) was treated with triethylamine (224 mL, 1.6 mol) and cooled to 0° C. Methanesulfonyl chloride (125 mL, 1.6 mol) was added keeping the temperature below 25° C. The mixture was stirred at 25° C. until complete and was then quenched with water (4 L) and stirred vigorously. The layers were separated and the aqueous layer was extracted with an additional 4 L of dichloromethane. The combined organic solutions were dried over sodium sulfate and concentrated in vacuo. The residue was dissolved in DMF (4 L), sodium azide (191 g, 2.94 mol) was added and the mixture was stirred and heated to 70° C. for 16 h, then allowed to cool to 25° C. Water (16 L) and diethyl ether (5.5 L) were added, the mixture was stirred vigorously and the layers were allowed to separate. The aqueous layer was extracted with diethyl ether (2×7 L), and the combined organic solutions were concentrated and the residue was eluted through silica (6 kg) with 1:3 ethyl acetate/hexane. Product containing fractions were concentrated in vacuo to yield S-9 (380 g, 84%) as an oil.

Preparation of (S)-1-(2-Aminopropyl)-6-hydroxyindazole (S-10). Ammonium formate (312 g, 4.96 mol) and 10% Pd(C) (38 g) were added to a stirred solution of S-9 (380 g, 1.24 mol) in 4 L of EtOH. After 2 h, another 38 g of 10% Pd(C) was added. The mixture was stirred for 2 h, then filtered through Celite, rinsing with EtOH, and the filtrate was concentrated. The residue was partitioned between saturated $NaHCO_3$ (4 L) and 1:1 ethyl acetate-THF (5 L). The aqueous phase was treated with 200 g of NaCl and extracted with 2:1 ethyl acetate-THF (3×4 L). The combined organic extracts were dried over sodium sulfate, filtered and concentrated in vacuo. The solid residue was suspended in ethyl acetate (3 L), stirred for 0.5 h and filtered to give 200 g of a solid. This material was suspended in THF (1 L) and the mixture was stirred for several minutes and filtered to give a solid, which was washed with cold THF (200 mL), air dried, and then dried for 16 h in vacuo at 45° C. to yield S-10 (183 g, 77%).

SCHEME 1

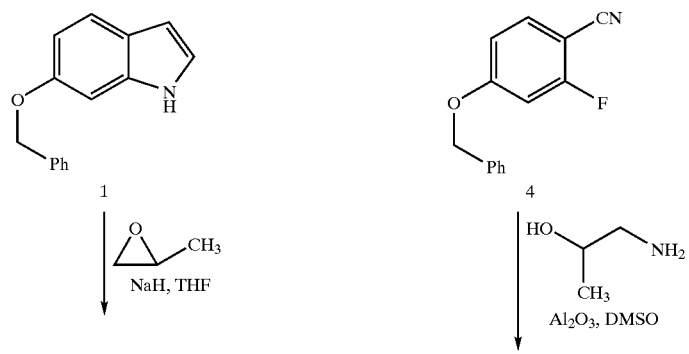

-continued

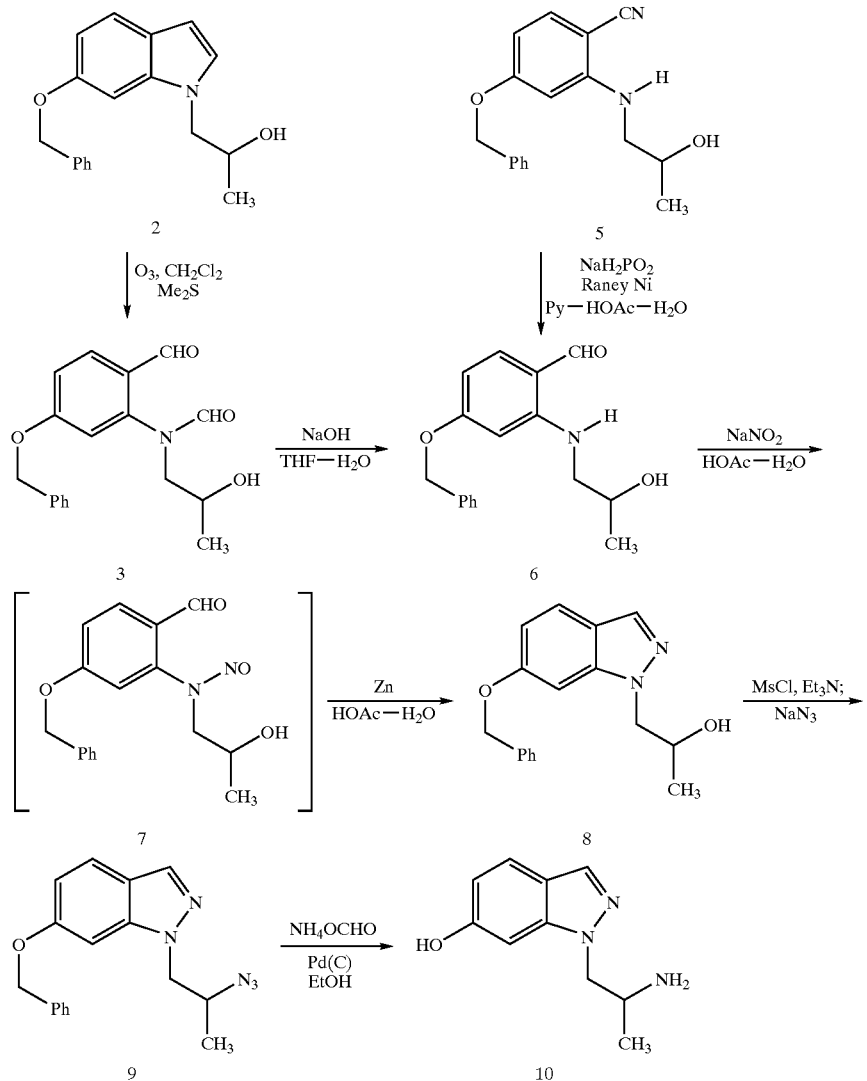

Other embodiments of the present invention will be apparent to those skilled in the art from consideration of the present specification and practice of the present invention disclosed herein. It is intended that the present specification and examples be considered as exemplary only, with a true scope and spirit of the invention being indicated by the following claims and equivalents thereof.

What is claimed is:

1. A method of making an indazole comprising:
   a) nitrosating a 2-aminobenzaldehyde to form a 2-nitrosaminobenzaldehyde,
   b) reacting the 2-nitrosaminobenzaldehyde with at least one reducing agent to form an indazole; and
   c) reacting the indazole with a sulfonyl halide or sulfonic anhydride to form a corresponding sulfonic ester.

2. The method of claim 1 wherein the amine group of the 2-aminobenzaldehyde in step a) is substituted with a hydroxyalkyl group and wherein the indazole formed in step b) is a 1-(hydroxyalkyl)indazole, the method further comprising converting the 1-(hydroxyalkyl) indazole into an 1-(aminoalkyl)indazole by the steps of:

d) reacting the corresponding sulfonic ester with a metal azide to yield a 1-(azidoalkyl)indazole; and e) reacting the 1-(azidoalkyl)indazole with a hydrogen source and a catalyst to yield 1-(aminoalkyl)indazole.

3. The method of claim 1, wherein the amine group of the 2-aminobenzaldehyde in step a) is substituted with a hydroxyalkyl group and wherein the indazole formed in step b) is a 1-(hydroxyalkyl)indazole.

4. The method of claim 1, wherein said reducing agent is a metal.

5. The method of claim 1, wherein said reducing agent is zinc.

6. The method of claim 2, wherein said catalyst is in the presence of at least one organic solvent.

7. The method of claim 6, wherein said organic solvent comprises ethanol.

8. A method of making an indazole comprising:
   a) nitrosating a 2-(hydroxyalkyl)aminobenzaldehyde to form a 2-(hydroxyalkyl)nitrosaminobenzaldehyde; and b) reacting said 2-(hydroxyalkyl)nitrosaminobenzaldehyde with at least one reducing agent to form a 1-(hydroxyalkyl)indazole.

9. The method of claim 8 further comprising:
c.) reacting the 1-(hydroxyalkyl)indazole with a sulfonyl halide or sulfonic anhydride to form a corresponding sulfonic ester;
d.) reacting the corresponding sulfonic ester with a metal azide to yield a 1-(azidoalkyl)indazole; and
e.) reacting the 1-(azidoalkyl)indazole with a hydrogen source and a catalyst to yield a 1-(aminoalkyl)indazole.

10. The method of claim 8, wherein said 2-(hydroxyalkyl) aminobenzaldehyde has the formula

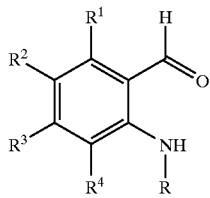

wherein
R is a $C_2$ to $C_{12}$ alkyl group substituted with at least one OH group and optionally substituted with phenyl, methoxyphenyl, (dimethylamino)phenyl, $OR^5$, $OC(=O)R^5$, $OC(=O)OR^5$, $N(R^5)_2$, $N(R^5)C(=O)R^5$, $N(R^5)C(=O)OR^5$, or with one or more F atoms; $R^1$, $R^2$, $R^3$ and $R^4$ are independently H, F, Cl, Br, $CF_3$, OH, $OR^5$, $OC(=O)R^5$, $OC(=O)OR^5$, $N(R^5)_2$, $N(R^5)C(=O)R^5$, $N(R^5)C(=O)OR^5$, $NO_2$, CN, $N_3$, SH, $S(O)_n R^5$, $C(=O)R^5$, COOH, $COOR^5$, $CON(R^5)_2$, $C_1$ to $C_6$ alkyl optionally substituted with phenyl, methoxyphenyl, (dimethylamino)phenyl, $C(=O)R^5$, COOH, $COOR^5$, $CON(R^5)_2$, CN, $OR^5$, $OC(=O)R^5$, $OC(=O)OR^5$, $N(R^5)_2$, $N(R^5)C(=O)R^5$, or $N(R^5)C(=O)OR^5$; or $R^1$ and $R^2$ as herein defined taken together form a ring, or $R^2$ and $R^3$ as herein defined taken together form a ring, or $R^3$ and $R^4$ as herein defined taken together form a ring; $R^5$ is $C_1$ to $C_6$ alkyl optionally substituted with phenyl, methoxyphenyl, (dimethylamino)phenyl, methoxy, ethoxy, benzyloxy, or with one or more F atoms, or $R^5$ is phenyl, methoxyphenyl, or (dimethylamino)phenyl; and n=0, 1, or 2.

11. The method of claim 8, wherein said reducing agent is zinc.

12. The method of claim 8, wherein said 2-(hydroxyalkyl) benzaldehyde is enantiomerically enriched.

13. The method of claim 9, wherein said catalyst is palladium on charcoal.

14. The method of claim 9, wherein said hydrogen source is ammonium formate.

15. The method of claim 9, wherein said 1-(aminoalkyl) indazole is enantiomerically enriched.

16. The method of claim 10, wherein R is 2-hydroxypropyl.

17. The method of claim 10, wherein R is (R)-2-hydroxypropyl.

18. The method of claim 10, wherein R is (S)-2-hydroxypropyl.

19. The method of claim 10, wherein $R^1$, $R^2$ and $R^4$ are H, and $R^3$ is benzyloxy.

20. The method of claim 10, wherein R is 2-hydroxypropyl, $R^1$, $R^2$ and $R^4$ are H, and $R^3$ is benzyloxy.

21. The method of claim 10, wherein R is (R)-2-hydroxypropyl, $R^1$, $R^2$ and $R^4$ are H, and $R^3$ is benzyloxy.

22. The method of claim 10, wherein R is (S)-2-hydroxypropyl, $R^1$, $R^2$ and $R^4$ are H, and $R^3$ is benzyloxy.

* * * * *